United States Patent [19]
Perelman et al.

[11] Patent Number: 6,070,583
[45] Date of Patent: *Jun. 6, 2000

[54] OPTICAL IMAGING OF TISSUE USING INELASTICALLY SCATTERED LIGHT

[75] Inventors: Lev T. Perelman, Malden; Jun Wu, Cambridge; Yang Wang, Sommervile; Ramachandra Roa Dasari, Lexington; Irving Itzkan, Boston; Michael S. Feld, Newton, all of Mass.

[73] Assignee: Massachusetts Institute of Technology, Cambridge, Mass.

[*] Notice: This patent is subject to a terminal disclaimer.

[21] Appl. No.: 08/391,209

[22] Filed: Feb. 21, 1995

[51] Int. Cl.⁷ .................................................. A61B 6/00
[52] U.S. Cl. ................................... 128/665; 128/633
[58] Field of Search .................... 128/664, 665, 128/633, 634; 356/433, 435, 342, 343, 338, 432; 250/330, 331, 332, 333, 334, 574, 575, 358.1

[56] References Cited

U.S. PATENT DOCUMENTS

5,371,368  12/1994  Alfano et al. .................. 250/341.1
5,421,337   6/1995  Richards-Kortum et al. ...... 128/665
5,467,767  11/1995  Alfano et al. .................... 128/665

Primary Examiner—Marvin M. Lateef
Assistant Examiner—Eleni Mantis Mercader
Attorney, Agent, or Firm—Hamilton, Brook, Smith & Reynolds, PC

[57] ABSTRACT

The present invention relates to the use of inelastically scattered light, particularly fluorescent and Raman scattered light, for determining the location and composition of material within various organs of the human body. The systems and methods of the present invention provide for medical imaging in three dimensions as well as histological information that can be used for diagnosing disease and various medical conditions.

20 Claims, 8 Drawing Sheets

OPTICAL IMAGING OF TISSUE USING INELASTICALLY SCATTERED LIGHT

This invention was made with government support under Grant Number NIH-5-P41-RR02594 awarded by the National Institutes of Health. The government has certain rights in the invention.

BACKGROUND OF THE INVENTION

The present invention relates to medical and diagnostic imaging systems and procedures. Clinical procedures currently employ a number of systems for locating, imaging and diagnosing various structures within the human body. These include x-ray computer tomography, ultrasound, and magnetic resonance imaging, among others. These systems are used to detect morphologic abnormalities associated with specific diseases or conditions in various body organs.

In the case of x-ray computer tomography, for example, a number of projection data are taken sequentially at different angles and the data are used to reconstruct an image of the object being scanned in three dimensions.

A continuing need exists, however, for further improvements in the field of tomographic imaging for medical applications including enhanced resolution, reduced cost and complexity, and improved diagnostic capability.

SUMMARY OF THE INVENTION

The present invention relates to the use of inelastically scattered light for locating, imaging and diagnosing structures within organs of the human body. In particular time-resolved photon migration is used for medical imaging, including optical methods for localizing lesions within the body. Since biological tissue is highly scattering, the problem in one of imaging an object embedded in a turbid medium. Most existing techniques use differences in the absorption or elastic scattering properties between the embedded object and its surroundings. In many cases of medical interest, however, the resulting contrast is relatively small, which severely limits the sensitivity and resolution.

Fluorescence spectroscopy studies of human tissue indicate that a variety of lesions show distinct fluorescence spectra compared to those of normal tissue. Thus, intrinsic tissue fluorescence can provide enhanced contrast, as well as diagnostic-histochemical information. In addition, exogenous dyes, many of which are known to fluoresce with high quantum yield, have been shown to exhibit selective uptake in neoplastic lesions. Use of such agents provides fluorescent markers with high quantum yields, and are used to locate embedded lesions in the breast, brain and other organs.

In a preferred embodiment of the present invention time-resolved optical tomography, and fluorescence and Raman spectroscopy, are used in combination to provide both spatial and chemical information about embedded objects in tissue. By measuring and analyzing the early portion of the fluorescence signal from embedded lesions for example, which rises rapidly and is not sensitive to fluorescence lifetime, precise timing information and hence accurate spatial resolution of embedded lesions can be obtained. A streak camera is used as a multichannel time-resolved detector, to obtain images of embedded fluorescent objects in a single measurement or in a sequence of measurements at one or more angles relative to the tissue.

Optical collectors positioned about the object to be imaged are used to collect fluorescence and/or Raman light scattered by the tissue in response to laser irradiation. The fluorescence and Raman data can be used to locate and image embedded lesions in three dimensions as well as provide information regarding the chemical composition of such lesions. This information can be used to identify such lesions as normal or abnormal, cancerous or precancerous etc. Further details regarding the use of induced fluorescence of tissue to diagnose cancer or precancerous lesions can be found in U.S. Ser. No. 08/219,240 filed on Mar. 29, 1994, the entire contents of which is incorporated herein by reference. The use of laser induced Raman spectroscopy of tissue for diagnosing various diseases and conditions is described in greater detail in U.S. Ser. No. 08/107,854 filed on Aug. 26, 1993 and having an international filing date of Jan. 17, 1992, and entitled Systems and Methods of Molecular Spectroscopy To Provide For The Diagnosis of Tissue, the entire contents of which is incorporated herein by reference.

Another preferred embodiment utilizes back-scattered fluorescent and Raman data to provide measurements of depth and lateral position of lesions in tissue. Fiber optic probes used for back scattering measurements are described in conjunction with the above referenced incorporated applications.

The above and other features of the invention including various novel details of construction and combinations of parts will now be more particularly described with reference to the accompanying drawings and pointed out in the claims. It will be understood that the particular system and methods embodying the invention are shown by way of illustration only and not as a limitation of the invention. The principles and features of this invention may be employed in varied and numerous embodiment without departing from the scope of the invention.

DETAILED DESCRIPTION OF THE INVENTION

Figure 1A:
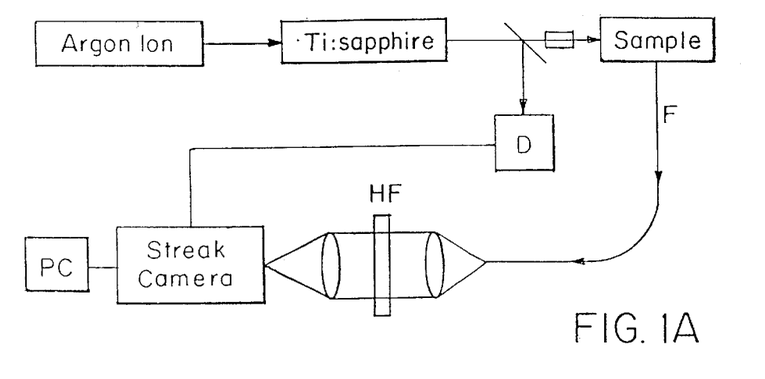
FIG. 1 is a schematic diagram of a tomographic apparatus where O is an embedded fluorescent object; D is a fast photodiode; F are collection fibers; HF is a holographic notch filter.
Figure 1B:
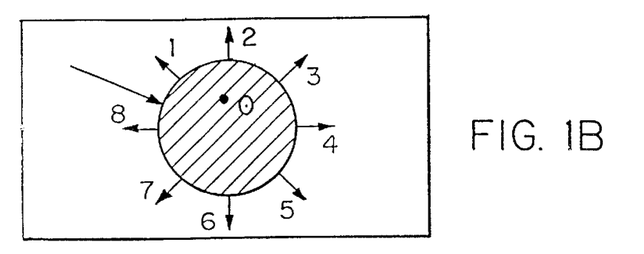

A schematic diagram of apparatus in accordance with the invention is presented in FIG. 1. The system can use ~150fs excitation pulse generated by a Coherent Mira 900 mode-locked Ti:sapphire laser pumped by a Coherent Innova 400 multiline argon ion laser, and a streak camera detection system consisting of a temporal dispenser C1587, synchroscan streak unit M1955 and tuning unit M1954 available from Hamatsu Photonic Systems Corporation. The wavelength in the present embodiment is 750 nm, the repetition rate 76 MHz, and the average power 1.5 W although other wavelengths rates and power levels can be used. A small portion of the excitation light, deflected by a quartz plane to a fast photodiode (D), was used as the optical triggering signal. Eight 100 μm core diameter optical fibers (F) were used to collect the fluorescence light and transmit it to the entrance slit of the steak camera. A Kaiser 752 nm holographic notch filter (HF) and two 780 nm long-pass filters were used in front of the streak camera to completely remove the excitation ligth. the system resolution, 10 ps, was determined by the intrinsic response of the streak camera, and temporal dispersion through the optical fibers, and optical trigger jitter.

Signals can be collected by 8 fibers evenly positioned around the circumference of the medium in the plane containing the fluorescence object (O). Differences in length among the fibers can cause uncertainties in the zeroes of time, but these can be calibrated out. In this arrangement, as shown is FIG. 1, the fluorescence return signal to be received earliest by the distal end of fiber 2, which is closest to the fluorescent object, and latest by fiber 6, which is furthest away. The proximal ends of these fibers can be arranged in a line and imaged onto the streak camera slit. The streak camera was used as both a time-and spatial-resolved multichannel detector. Signals from different fibers appeared at different vertical locations on the CCD array of the streak camera, and the temporal information was displayed horizontally a data processor or personnel computer (PC) receives image data from the streak camera and determines the location of material within the tissue.

Figure 2:
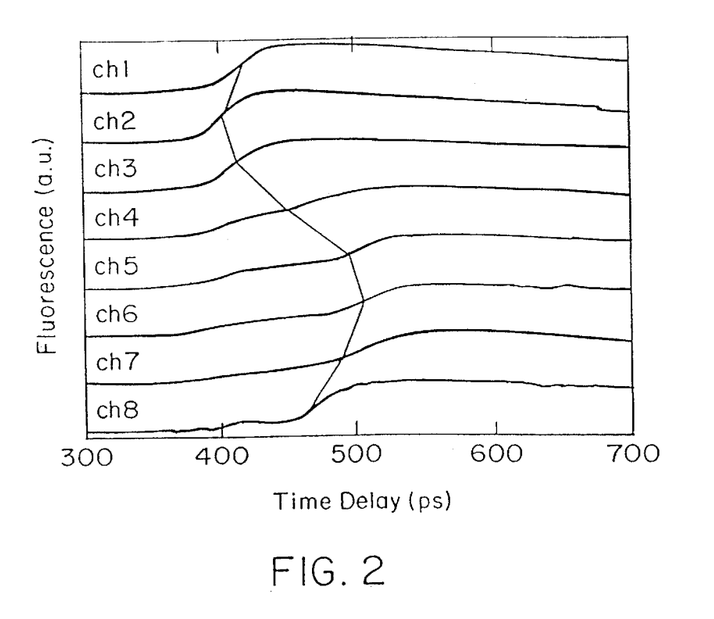
FIG. 2 is an 8-channel time-resolved fluorescence signal observed by the streak camera where the line connects $t_{1/2}$ points of the eight channels.
Figure 3A:
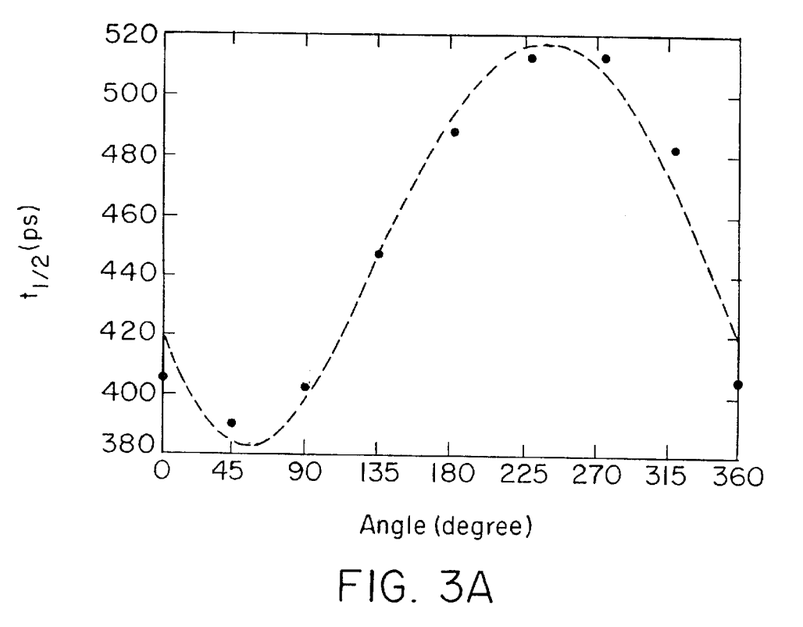
FIG. 3A is a graphical representation where fluorescence signal detected by each individual fiber surrounding the object containing a single embedded object. Fits using a triangulation procedure are plotted as dashed curves.
Figure 3B:
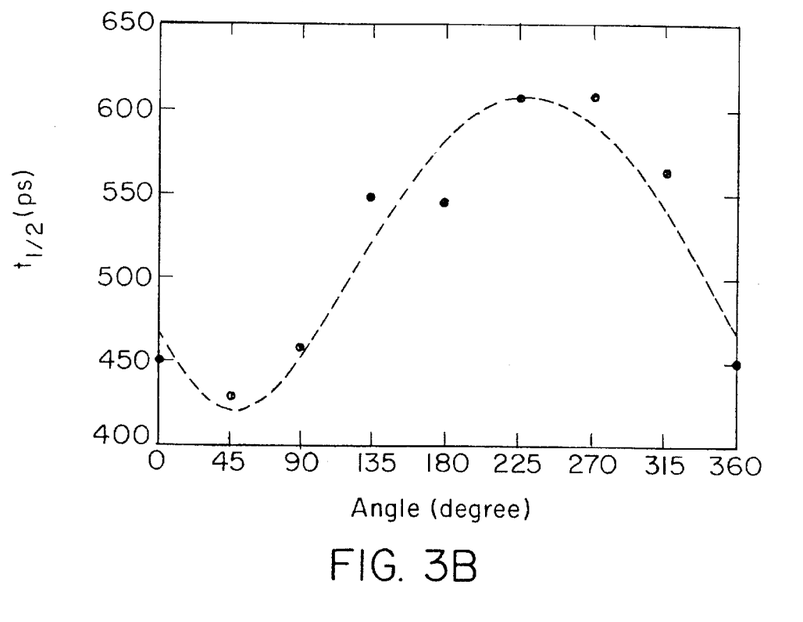
FIG. 3B is graphical representation similar to that of FIG. 3A with a lower mean free path.

A typical 8-channel time-resolved fluorescence signal is shown in FIG. 2. The rising edge of each curve contains timing information which can be used to extract spatial information. The exact timing of these rising edges can be determined in several ways. In the present method the time at which the signal reaches half-maximum of that channel, $t_{1/2}$ was selected at the representative time for each curve. In FIGS. 3A and 3B we plot $t_{1/2}$ for each collection fiber for a single embedded object for the cases of 1.8 and 0.9 mm scattering mean free path (mfp, $1/\mu_s$), respectively. The collection time is 5 minutes in the example, but can be longer or shorter depending on the object to be imaged. The local minimum indicates the position of the object. Similar data were obtained for mfp's between 0.6 and 3.6 mm. (Note that the diameter of the sample is equivalent to 20–120 mfps).

In order to extract the spatial location of the embedded fluorophore, in this procedure it is assumed that the time delay for the early photons is proportional to the distance traveled. In our cylindrical geometry, this can be expressed as $$T_n \sqrt{R^2 + r^2 - 2rR\cos(\theta - \theta_n)},$$

with R the radium of the sample, $\theta_4$ the angular location of the nth channel, and (r, θ) the polar coordinates of the embedded fluorophore. The spatial location of embedded objects can be obtained by fitting the experimental data (e.g. FIGS. 3A and 3B) using Eq. (1) Typical fits are shown as dashed lines in FIG. 3A and 3B.

Figure 4:
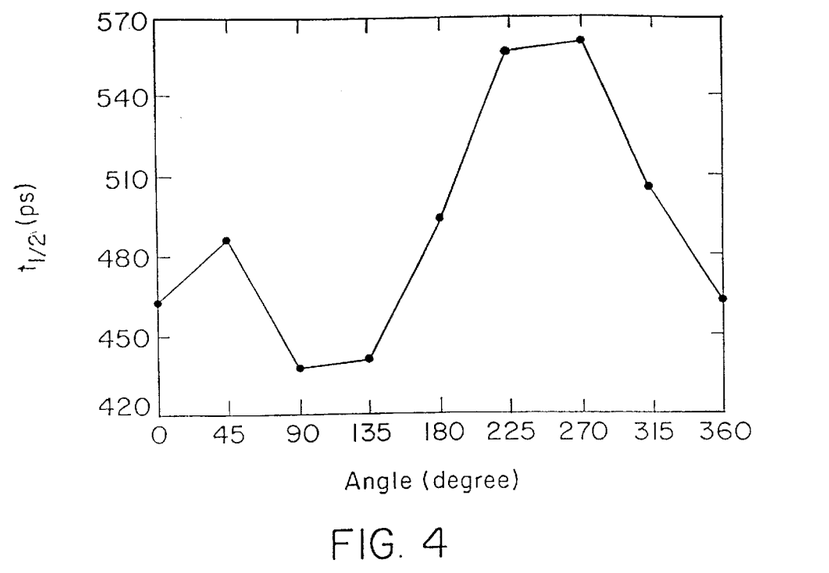
FIG. 4 is a graphical representation where $t_{1/2}$ is the fluorescence signal detected by each individual fiber surrounding a medium containing two embedded objects.

To illustrate the measurement of two embedded objects in which the scattering mfp was 1.8 mm, FIG. 4 plots $t_{1/2}$ for each collection fiber with two objects present. Each local minimum represents a single fluorescing object. Use of more than eight fibers improves the resolution particularly when measuring a number fluorescing objects. The inverse problem in this case is more complicated and requires an accurate theoretical model of the photon migration process in a turbid medium described in greater detail below.

This geometry is applicable to many human organs, such as brain and breast. Furthermore, this method can be extended to other geometries, as well. Note that with fibers positioned in different planes, objects can be localized in three dimensions. In addition, by observing fluorescence at multiple wavelengths, one can obtain histochemical information.

The steak camera photoathode-window (s–20/UV, spectral response from 200–850 nm) can be more nearly matched to our fluorescent wavelength or wavelengths depending on the fluorescence wavelengths of interest. In addition, the system throughput can be improved by replacing the above fibers with single-mode optical fiber bundles of larger diameter, e.g., 1 mm, without loss of temporal resolution. Improving these factors increases the signal-to-noise ratio by factor of several hundreds, which permits reduction of the excitation power and/or collection time. The localization accuracy comparable to that of the data presented here can be obtained from a 5 mm diameter fluorescent object containing hematoporphryn derivative (HpD) at clinical concentrations using excitation power of a few tens of mW and less than one minute accumulation time.

In another preferred embodiment the rise-time of fluorescence provides precise timing information, hence accurate spatial resolution, of an embedded object in tissue. Electronic excitation occurs on the optical time scale; and the rise time, which is not affected by fluorescence decay, is on the order of $10^{-13}$ seconds. Raman scattering another potential source of high contract, exhibits comparably rapid rise times and can be used for precise timing. Note that these spectroscopic techniques carry the additional potential advantage to provide histochemical information about the object to be imaged. Thus fluorescence emission and Raman scattering are used to obtain time-resolved and three-dimensional spectroscopic information of lesions through overlying tissue.

Figure 5A:
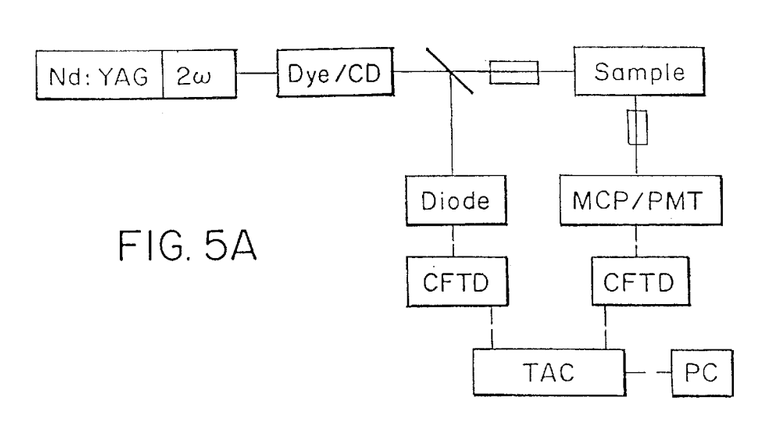
FIG. 5 illustrates a schematic diagram showing instrument components where CD: cavity dumper; MCP/PMT: microchannel plate/photomultiplier tube; CFTD: constant fraction time discriminator; TAC: time-to-amplitude converter. Solid lines represent optic signal paths and dashed electronic signal paths. The insert shows the arrangement of excitation and collection probes, and the sample geometry.
Figure 5B:
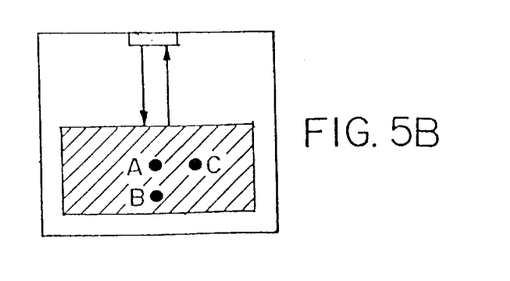

The present embodiment can use few-ps pulses for excitation and time-resolved single-photon counting for detection. The wavelength is 570 nm, the repetition rate 1 MHz and the average power 30 mW. The apparatus is illustrated in FIG. 5. A 10 nm bandpass filter (centered at 610 nm) and a 600 nm long pass filter in front of the detector completely remove the excitation light. The temporal resolution of the system, about 80 ps, is mainly due to the transit time spread of the PMT. This is adequate to resolve the photon migration signals in our photon samples.

In our singled-ended probing geometry a collection fiber is positioned adjacent to the incident beam on the same surface of the tissue, and the fluorescence material is located at a fixed distance within the tissue. In this geometry the earliest arriving fluorescence photons emitted from the fluorescing material or lesions returns to the collection fiber sooner than those from a second lesion B, located at a greater depth, or a third lesion C, laterally displaced from A. This illustrates the use of a fiberoptic probe in determining the location of the fluorescent object in three dimensions by observing the time-resolved fluorescence signal. Ultrafast time-gating can further improve spatial resolution.

Figure 6A:
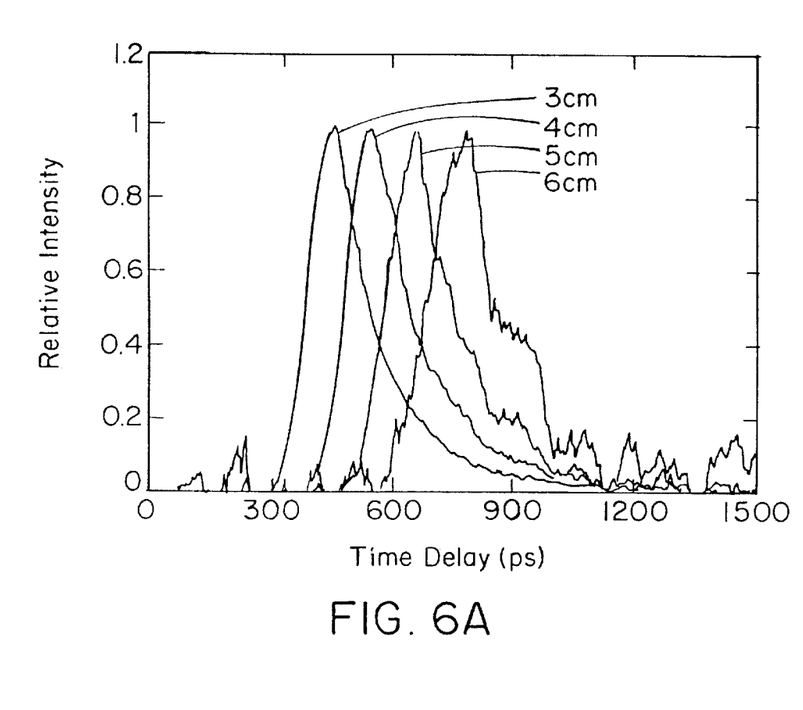
FIG. 6A graphically illustrates a fluorescence emission from RB dye cell at four different depths.
Figure 6B:
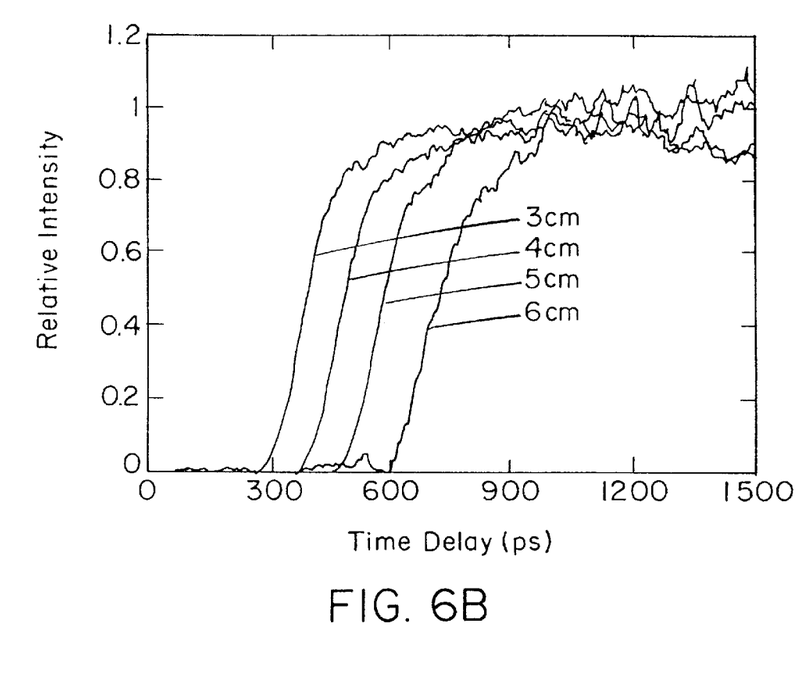
FIG. 6B is a graphical illustration similar to that of FIG. 6A with an R6G dye cell.

Fluorescence can be used to provide time-of-flight signals for ranging, despite the long fluorescence lifetimes, typically on the order of a few ns, relative to the photon migration time of interest. To illustrate this, we compared the time-resolved signals emitted from dye cells embedded in a polystenryl suspension containing either RB (in water lifetime 130 ps) or R6G (lifetime 3.9 ns). The dye cell depth was changed from 3 to 6 cm in 1 cm increments. The scattering mean free path (mfp) was 4 mm. The results are plotted in FIGS. 6A and 6B. In spite of the fact that the fluorescence lifetimes of Rb and R6G differ by a factor of 30, the rising edges of these two sets of curves are extremely similar. In fact, they closely represent the rising edge of the photon migration curves.

Figure 7:
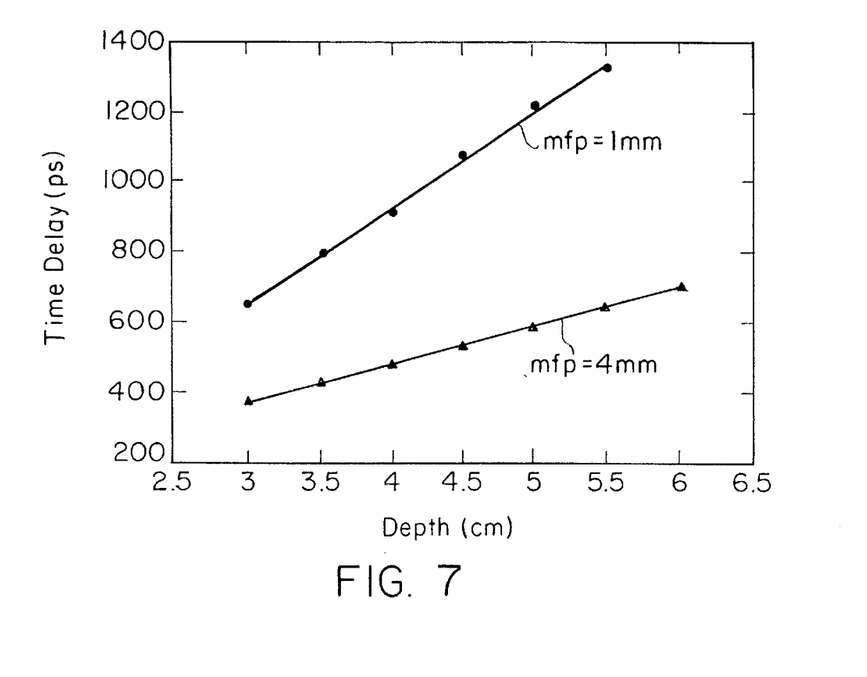
FIG. 7 graphically illustrates the depths of a fluorophase vs. $t_{1/2}$ for two different scattering coefficients.

The depths of a fluorescent object can be easily probed in the backscattering geometry by looking at the earliest-arriving fluorescence photons, even under strong scattering conditions. The time-of-flight for these earliest arriving photons is proportional to twice the depth of the fluorescent object. As expected, fluorescence emitted from a deeper object arrives at the detector later in addition, increased scattering also delays the arrival time, as shown in the plot of depths vs. time, of FIG. 7. The time at which the signal reaches half maximum, $t_{1/2}$ is used as the representative time for each curve. The spatial resolution is determined by both the intrinsic factor, due to the statistics of photon migration, and extrinsic factors such as the sensitivity of the detector and signal-to-noise (S/n) level. With five-minute accumulation time the current set-up can resolve a depth of 1 mm, even at a distance of 100 mfp's.

Figure 8:
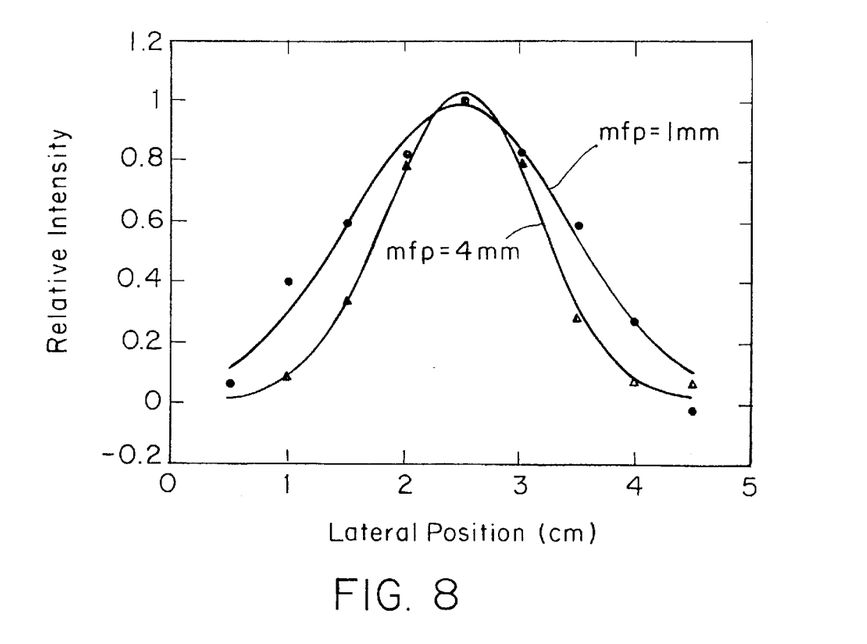
FIG. 8 graphically illustrates lateral location of a fluorophore using ultrafast time-gating for two different scattering coefficients.

To obtain lateral information about an embedded object, we measured the time-resolved fluorescence signals as a function of the lateral position of the dye cell at depth of 5 cm. Based on simple geometrical considerations, we expect lateral resolution to be poorer than depth resolution. However, lateral resolution can be improved by using an ultrafast time window for the earliest arriving photons, which is similar to the typical time-gate transillumination imaging experiments. The optimum time gate was chosen based on considerations of both resolution and S/N a ratio. Typically, we used a 24 ps time window. FIG. 8 plots the time gated intensity vs. the lateral displacement of the fluorescence dye cell at 25 and 100 mfp's, respectively. A lateral resolution of 1 cm is obtained with this time window, however, much greater resolutions can be obtained.

Figure 9:
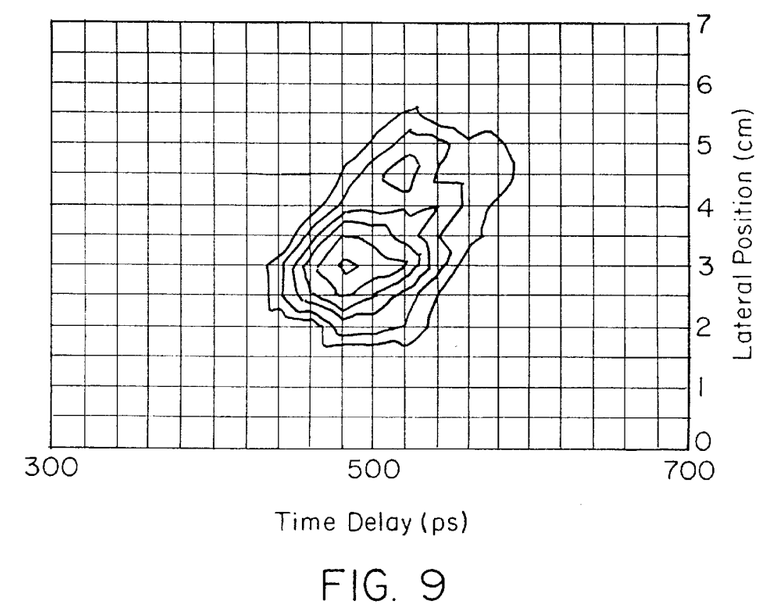
FIG. 9 graphically illustrates the probing of two identical fluorophores at different depths.

Measurements were made with two embedded cells containing the same fluorescence dye. The two objects were positioned 1.8 cm apart at depths of 4.5 and 5 cm, respectively. Using lateral displacement and time delay as variables, we can construct a contour map of the time-derivative of the time-resolved intensity (FIG. 9). The time-derivative, a measure of how fast the time-resolved signal evolves, reaches a maximum at approximately $t_{1/2}$, which in turn provides the depth information. Although the signal from the shallower object dominated, the 3-d positions of both objects can be ascertained. This is because different time-gating can be used to provide different depth measurements inside the tissue of medium. Note that although the lateral dimension represents the actual image of the object, longitudinally (i.e., temporally) it only provides information about the top surface of the fluorescent material. Also note that the best lateral resolution is obtained at the earliest time gate, i.e., where the contours begin along the time axis.

Figure 10A:
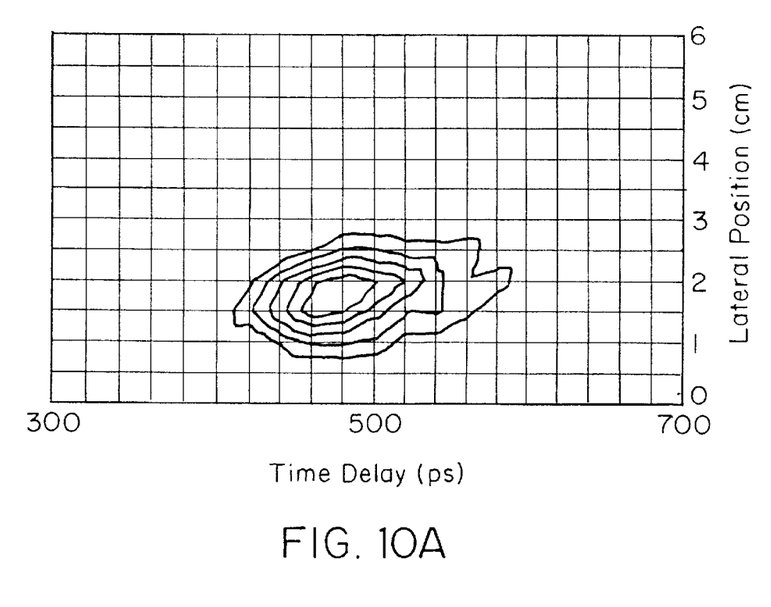
FIG. 10 graphically illustrates the probing of two different fluorophores detected at 620 nm (a) and 670 nm (b).
Figure 10B:
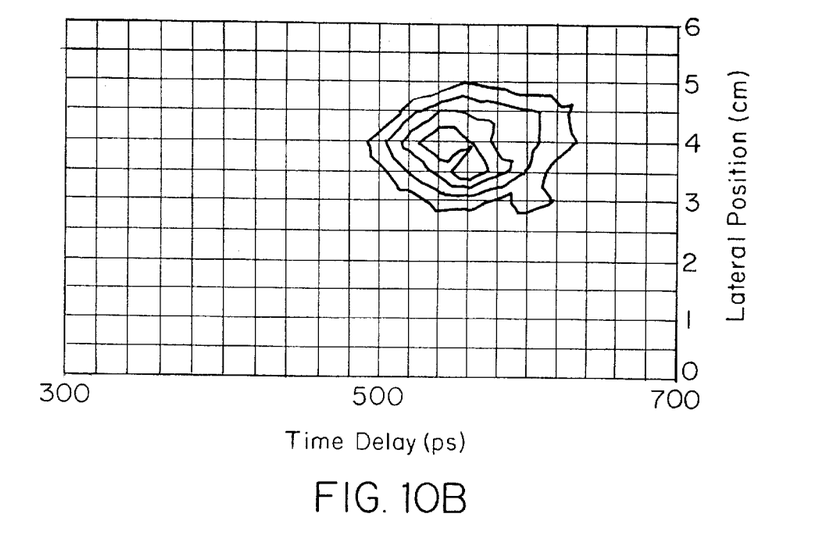

If the two embedded objects have distinct spectroscopic features, imaging capability can be enhanced. This was demonstrated by measuring the fluorescence intensity from two cells (similar geometry as in FIG. 9) containing S640 and HIDCI, respectively, at 620 and 670 nm (FIG. 10) by placing a spectrometer in front of the PMT. Compared to FIG. 9, signal interference between the two objects is reduced, and more importantly, the chemical identities of the objects can be obtained.

Figure 11:
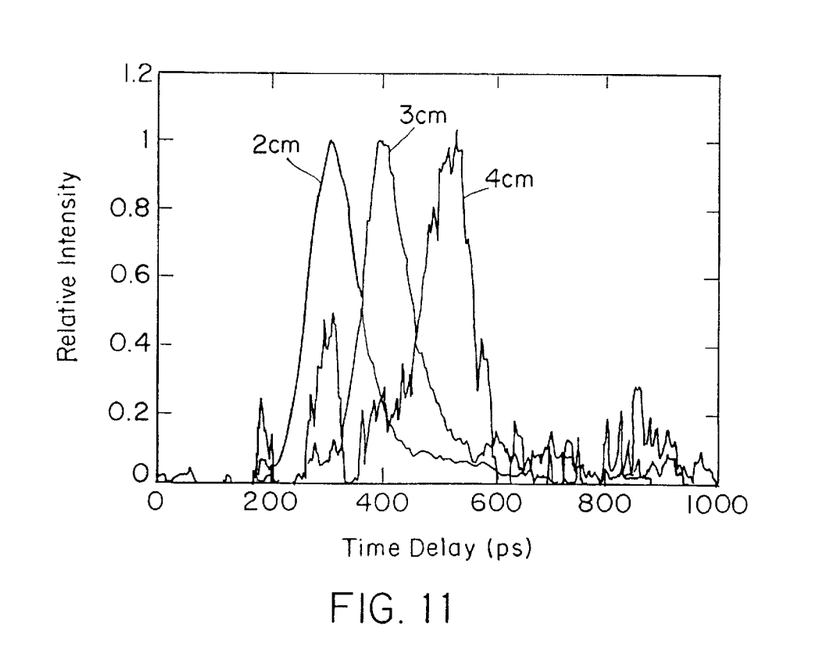
FIG. 11 graphically illustrates results with Raman scattering from β-carotene cell at three depths.

A Raman scattering cell containing β-carotene having a Raman vibration at 1157 $cm^{-1}$ was studied. To establish that the detected signals were from Raman scattering rather than fluorescence from either β-carotene or sample impurities, in a measurement without the scattering medium, the time-resolved Raman scattering was identical in shape to that of the laser light (determined by instrumental resolution), obtained by deflecting part of the laser beam into the fiber probe and removing the filters. This is consistent with the instantaneous nature of Raman scattering. The possibility of laser light leakage was excluded by replacing the Raman cell with a Raleigh scattering cell containing KI powder, which does not have Raman bands about 300 $cm^{-1}$. As a further check, the emission spectrum from the Raman sample was collected using standard fluorimeter with the same 570 nm excitation. Distinct Raman peaks at 605, 610 and 624 nm, which correspond to the known Raman shifts of 1008, 1157 and 1516 $cm^{-1}$ for β-carotene, were observed with minimum background. FIG. 11 displays the time-resolved Raman signal for cell depths of 2, 3 and 4 cm in a scattering medium with 7 mm mfp.

Thus time-resolved fluorescence emission can be used as a probe to provide accurate information about the position of an object such as a lesion embedded in a turbid medium such as tissue, despite the long fluorescence decay time. The time evolution of the signal is determined by both the time-course of the photons migrating through the scattering media and the decaying fluorescence. These measurements establish that the early portion of the signal rises rapidly and is not sensitive to the relative long fluorescence lifetime. The early portions of both the fluorescence and Ramans signals thus represent the actual time-of-flight of photons traversing the scattering medium. In the case of fluorescence, this is due to the fact that electronic excitation from the ground state to the excited states is extremely rapid, on the order of $10^{-13}$ second, so that the rising edge of the fluorescence lifetime curve is effectively a step function. The resulting signal, a convolution of the distribution of the time-of-flight of photons migrating to the detector and the fluorescence decay curve, is mainly determined by that of the time-of-flight curve. In addition, these earliest arriving photons undergo minimal scattering, resulting in high spatial resolution. In other words, by measuring and analyzing the earliest-arriving photons, this serves to minimize the uncertainties due to both diffusive scattering the finite fluorescence lifetime.

However, unlike many existing trans-illumination methods, a backscattering geometry with single-ended detection is employed. In this configuration, the isotropic fluorescence emission or Raman scattering events serve to reverse the direction of nearly straight photon paths. The earliest signals observed in this case are proportional to twice the distance from the sample surface to the location of the embedded objects, which in our experiments are composed of molecules having unique fluorescence or Raman scattering characteristics. Thus, the arrival time of the earliest photons can provide the depth information of the embedded objects, as well as the usual 2-D localization. In addition, lateral spatial resolution can be optimized by using a short duration time-gate to select the earliest arriving photons. Also, note that in a turbid medium, a backscattering geometry cannot be used with a technique based on elastic scattering or absorption, because photons backscattered by the medium will mask the signals arising from the embedded object.

With the technique presented in this paper, either native tissue chromophores or exogenous dyes can be used to detect embedded lesions. In the former case, both biochemical and spatial information about the lesion are provided simultaneously. The contrast between diseased and normal tissue can be enhanced by utilizing these properties instead of absorption or elastic scattering, and diagnostic information can be obtained. Exogenous dyes, which are known to exhibit fluorescence with high quantum yield, can also be used as a source of contrast. For example, a number of known methods use selective uptake of photosensitizing agents, such as ameotoporphrin derivative, in neoplastic lesions. Use of such agents would provide fluorescent markers with high quantum yields which could serve to locate embedded lesions in the breast, brain or perhaps other organs.

Multichannel detection can be used to extend the capability of the technique presented here in several ways. An optical fiber array can be utilized to obtain 3-D information in a single measurement by displaying physical position along one axis and time along the other. Further more, with the aid of a spectrograph, real-time spectroscopy and optical tomography can be achieved by simultaneously displaying spectral and temporal information.

To understand the differences between prior methods and the present invention it is helpful to consider a system in which Photons propagating through a turbid medium from point A to point B can be described using statistical considerations. A photon originating at point A is elastically scattered multiple times, each time being defected into a particular angle with a well-defined probability, thus forming a trajectory within the medium. Each trajectory has a particular probability. By calculating this probability and then summing over all possible trajectories, one obtains the probability for the photon to travel between two points in the medium.

The probability for a photon to traverse the scattering medium from point A with radius-vector $r_A$ to point B with radius-vector $r_B$ in a time interval T can be written as a path integral:

$$P(r_A, r_B, T) = \int \mathcal{D}r(t) \exp\left\{-\frac{1}{2\mu_s(1-g)} \int_0^T \dot{r}(t)^2 dt\right\} J[\dot{r}(t)], \quad (2)$$

where the function $$J[\dot{r}(t)] = \int \mathcal{D}\Omega(t) \exp\left\{i\mu_s \int_0^T dt \Omega(t)(\dot{r}(t)^2 - 1)\right\}$$

insures that photons propagate at the speed of light in the medium (c=1) at every point along the trajectory, and $$\mathcal{D}r(t) = \prod_{n=1}^N dr_n.$$

Integral (2) represents the solution of the equation of radiative transfer for the case in which elastic scattering is described by a Gaussian phase function.

The probability distribution function for the case of isotropic scattering, generally referred to as the diffusive limit, does not follow immediately from Eq.(2), which was derived in the approximation of small angle scattering. However the diffusive limit can be calculated by eliminating the angular dependence of the phase function. Thus, in this case $P(r_A, r_B, T)$ is a path integral over the function $J[r(t)]$:

$$P(r_A, r_B, T) = \int_A^B \mathcal{D}r(t) J[\dot{r}(t)]. \quad (3)$$

By writing the trajectory in the form of a Fourier sine series with a fundamental period of T, an approximate expression for Eq. (3) can be derived:

$$P(R, T) = \begin{cases} 0, & R > T \\ F(T)\left(1 - \frac{R^2}{T^2}\right)^{\frac{3\mu_s T}{4}}, & R < T, \end{cases} \quad (4)$$

where $F(T) = \dfrac{2}{T^3 B(3/2, 3\mu_s T/4 + 1)}$ and $B(\alpha, \beta)$ is the beta function. This integral takes on different values for T<R and T>R. Note that for T<R the probability (3) is equal to zero, which simply reflects the requirement of causality—there is not enough time for a photon initially at A to get to point B. When R<<T we immediately obtain $$P(R, T) \cong \left(\frac{3\mu_s}{4\pi T}\right)^{3/2} \exp\left\{-\frac{3\mu_s R^2}{4T}\right\}. \quad (5)$$

This formula is a standard result of the time dependent diffusion approximation. In contrast Eq. (4) has the correct properties for times R~T.

A much more important and interesting case for which the scattering is not isotropic and the phase function is highly peaked in the forward direction. This is the case of relevance to biological tissue. The solution to the transport equation for a sample of infinite extent is given by the integral Eq. (2). Thus:

$$P(r_A, r_B, T) = \int_{-\infty}^{+\infty} d\omega \int \mathcal{D}r(t) Q \exp\left\{-\int_0^T \left[\frac{1}{2\mu_s(1-g)}\dot{r}(t)^2 - i\omega(\dot{r}(t)^2 - 1)\right] dt\right\}. \quad (6)$$

The same approach employed in the diffusive limit can be used to evaluate this integral. Calculations show that the probability depends upon the two factors, one resembling the "diffusion" term which dominates in the long time limit, and the second, which comes into play at short times, and is most important for the early photons that follow short, "almost straight" trajectories.

The measurements used ~150 fs excitation pulses generated by a mode-locked Ti:sapphire laser pumped by a multiline argon ion laser, and a streak camera detection system. The incident wavelength was 800 nm, the repetition rate 76 MHz, and the average power 1.5 W. A small portion of the excitation light, deflected by a quartz plate to a fast photodiode, was used as the optical triggering signal. transmission signals were collected by a 200 µm core diameter optical fiber. The other end of the fiber was imaged onto the streak camera slit. The system resolution, 10 ps, was determined by the intrinsic response of the streak camera, the temporal dispersion through the optical fibers, and optical trigger jitter.

Figure 12:
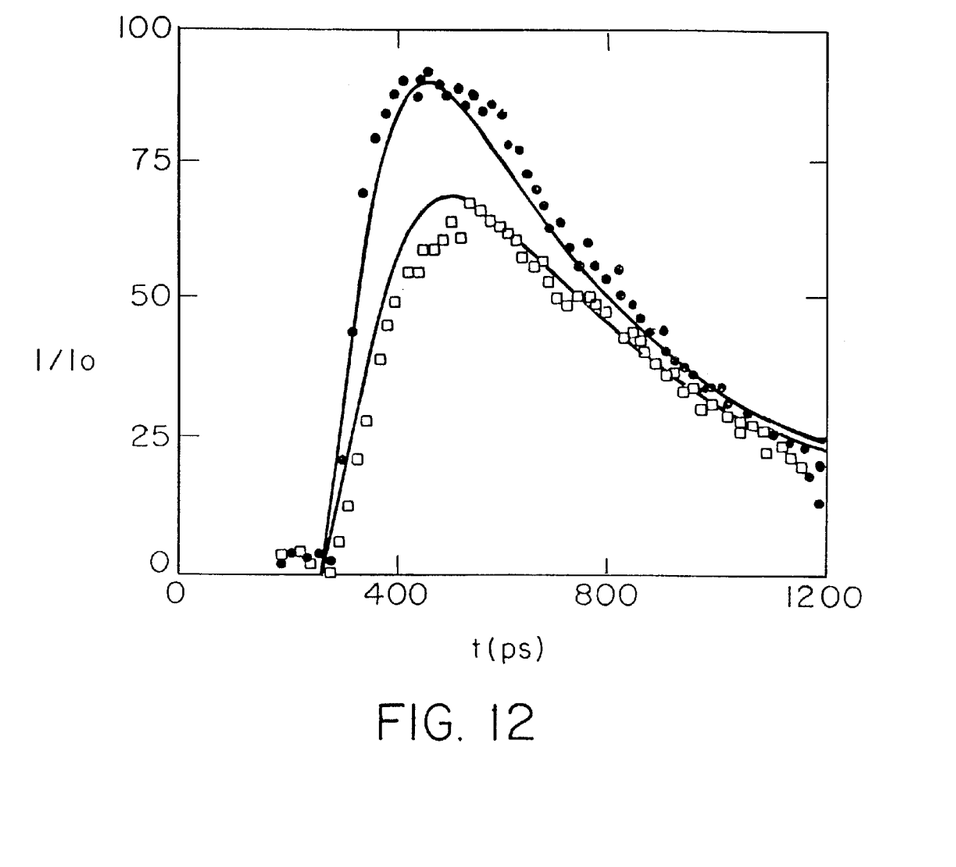
FIG. 12 graphically illustrates time resolved measurements of a turbid medium.

Comparison of experimental data with the theoretical predictions that follow from Eq. (6). As shown in FIG. 12 results indicate agreement between theory and experiment that can be obtained by varying only one parameter, the scattering coefficient $\mu_s$. This agreement exists not only for decreasing ("diffusive"), part of the curve but also for the initial part of the curve that represents the earliest highly "non-diffusive" photons. Moreover, FIG. 12 suggests that Eq. (6) has the correct angular dependence.

FIG. 12 shows time-resolved signal measurements for transmission through a slab of turbid media (Intralipid with concentration $C_{Intr}$+10 ml) of thickness L=5.5 cm. The probe was displaced laterally 2 cm from the incident laser beam. Two curves represent two different angles of the probe, θ=40° and θ=−40° measured with respect to the direction of the incident beam. The experimental data points are compared with theory (solid lines) with $\mu_s$=3cm$^{-1}$, g+0.8.

Equivalents

While the invention has been described in connection with specific methods and apparatus, it is to be understood that the description is by way of example and not as a limitation to the scope of the invention as set forth in the claims.

We claim:

1. A method for determining a location of material within tissue comprising;
    irradiating tissue with radiation, the tissue having material located underneath a surface of the tissue;
    collecting inelastically scattered radiation from the material at a plurality of at least three locations on different sides of the tissue and defining a plane extending through the tissue; and
    determining the location of the material within the tissue.

2. The method of claim 1 further comprising providing a detector that detects the collected radiation and generating a three dimensional image of the material from the detected radiation from the material, the inelastically scattered radiation comprising fluorescent radiation.

3. The method of claim 1 further comprising detecting Raman scattered radiation from the material.

4. The method of claim 1 further comprising providing a plurality of optical collectors positioned around the tissue to collect light from the tissue.

5. The method of claim 1 further comprising providing a plurality of optical fiber, each having a distal end and a proximal end, the distal ends of the fibers being positioned about the tissue to collect light from the tissue.

6. The method of claim 1 further comprising detecting the collected radiation with a streak camera.

7. The method of claim 1 wherein the determining step further comprises measuring an increase in inelastically scattered radiation from the tissue as a function of time.

8. A method for determining a location of material within tissue comprising;
    providing a laser that emits light at an excitation wavelength;
    providing a plurality of optical collectors around the tissue and a detector, the collectors being optically coupled to the detector;
    irradiating tissue with radiation at the excitation wavelength, the tissue having a lesion located underneath a surface of the tissue;
    collecting inelastically scattered radiation from the lesion at least at three locations on different sides of the tissue, the three locations defining a plane extending through the tissue; and
    detecting with the detector the collected light;
    generating a three dimensional representation of the lesion with the detected light; and
    determining the location of the lesion within the tissue.

9. The method of claim 8 wherein the detector detects the collected radiation and generating a three dimensional image of the lesion from the detected fluorescent radiation from the material the inelastically scattered radiation comprising fluorescent radiation.

10. The method of claim 8 further comprising detecting Raman scattered radiation from the material.

11. The method of claim 8 further comprising providing a plurality of optical fibers positioned around the tissue to collect light from the lesion.

12. The method of claim 8 further comprising determining the presence of a fluorophore in the lesion.

13. The method of claim 8 further comprising determining a concentration of an analyte in the lesion.

14. The method of claim 8 further comprising measuring an intensity of radiation from the lesion as a function of time from the emission of the excitation wavelength.

15. The method of claim 8 further comprising:
    collecting fluorescent light from the tissue at least at three angles;
    detecting and comparing the time-dependent fluorescent light at each of the three angles; and
    forming an image of fluorescing tissue from the compared fluorescent signals and determining a depth of the tissue within the medium.

16. A tomographic system for determining a location of material within tissue comprising;
    a light source that emits an excitation wavelength of radiation, the light source being optically coupled to irradiate tissue with radiation, the tissue having material located underneath a surface of the tissue;
    an optical collector that collects inelastically scattered radiation from the material at least at three locations on different sides of the tissue, the three locations defining a plane extending through the tissue;
    a detector optically coupled to the optical collector; and
    a data processor that determines the location of the material within the tissue.

17. The system of claim 16 further comprising an image processor that generates a three dimensional image of the material from the detected radiation from the material, the inelastically scattered radiation comprising fluroescent radiation.

18. The system of claim 16 further comprising a filter for selectively transmitting Raman scattered radiation from the material.

19. The system of claim 16 wherein the optical collector comprises a plurality of optical fibers positioned around the tissue.

20. The system of claim 16 wherein the optical collector comprises a plurality of collectors that are positioned concentrically about the tissue.

* * * * *